United States Patent [19]
Davis et al.

[11] Patent Number: 5,429,633
[45] Date of Patent: Jul. 4, 1995

[54] FORM RETENTIVE ABSORBENT PADS

[75] Inventors: Martha Davis, New York, N.Y.;
Daniel Formosa, Montvale, N.J.;
Jeannie Gerth, Brooklyn, N.Y.;
Patricia A. Moore, Montvale;
Stephen Russak, Hoboken, both of
N.J.; Tamara Thomsen; Tucker
Viemeister, both of New York, N.Y.

[73] Assignee: McNeil-PPC, Inc., Milltown, N.J.

[21] Appl. No.: 949,751

[22] Filed: Sep. 23, 1992

Related U.S. Application Data

[63] Continuation of Ser. No. 549,337, Jul. 6, 1990, abandoned.

[51] Int. Cl.⁶ .............................................. A61F 13/15
[52] U.S. Cl. ............................... 604/387; 604/385.1; 604/402
[58] Field of Search .................... 604/385.1, 387, 393, 604/395, 398, 400, 402, 366–374

[56] References Cited

U.S. PATENT DOCUMENTS

| | | | |
|---|---|---|---|
| 4,315,507 | 2/1982 | Whitehead et al. | 604/387 |
| 4,773,905 | 9/1988 | Molee et al. | 604/378 |
| 4,865,597 | 9/1989 | Mason, Jr. | 604/366 |
| 5,197,959 | 3/1993 | Buell | 604/378 |

FOREIGN PATENT DOCUMENTS

| | | | |
|---|---|---|---|
| 0330206 | 8/1989 | European Pat. Off. | A61F 13/16 |
| 0331018 | 9/1989 | European Pat. Off. | A61F 13/16 |
| 0335527 | 10/1989 | European Pat. Off. | 604/387 |
| 0337438 | 10/1989 | European Pat. Off. | 604/387 |
| 0345703 | 12/1989 | European Pat. Off. | 604/387 |
| 0360285 | 3/1990 | European Pat. Off. | |
| 2438457 | 10/1978 | France | A47K 10/16 |
| 3326026 | 2/1985 | Germany | 604/389 |
| 2214085 | 8/1989 | United Kingdom | 604/387 |
| 2243283 | 10/1991 | United Kingdom | 604/387 |

*Primary Examiner*—Randall L. Green
*Assistant Examiner*—Rob Clarke

[57] ABSTRACT

Form retentive absorbent pads are disclosed which comprise fluid absorbent material and at least one bendable element which can be deformed by the user and which will retain its shape during use. The preferred embodiments, the bendable element provides at least a degree of conformation in the critical central area of the pad, most preferably at least in the longitudinal (y axis) direction. Conformability created in this area allows the user of the pad to mold the pad to the body to maximize comfort and fluid absorption. Preferred embodiments include bendable elements which form winglets which are bent around the edges of the undergarment to hold the pad in place during use.

23 Claims, 4 Drawing Sheets

FORM RETENTIVE ABSORBENT PADS

This is a continuation of application Ser. No. 549,337, filed Jul. 6, 1990, now abandoned.

BACKGROUND OF THE INVENTION

This invention relates to absorbent pads and, more particularly, to absorbent pads able to assume and maintain a variety of conformations.

Absorbent pads find many common uses, such as in the containment of bodily fluids. The ability of an absorbent pad to maintain close contact with a fluid-bearing surface is thus a key determinant of its efficacy in this regard. Diapers, bandages, and feminine hygiene products such as panty shields and sanitary napkins provide examples of absorbent pads employed in the containment of bodily fluids.

In addition, these and other types of absorbent pads are often designed for contact with highly-contoured surfaces such as those found on the human body. Given the great variation in shape between different portions of the human anatomy and the further, often pronounced, variation between different individuals with respect to even the same body region, the importance attached to the ability of such products to assume and maintain a variety of shapes becomes apparent.

Equally important in the containment of emanating fluids is the ability of an absorbent pad to maintain close proximity with the fluid-bearing surface. For example, it is known in the art that reasonably good placement can be obtained by affixing the napkin to the woman's undergarment, typically through the use of adhesives. Unfortunately, however, such attachment means are often subject to failure and, moreover, contribute nothing to the napkin's retention of a conformation closely approximating the unique and characteristic contours of the woman's physique.

It is accordingly an object of this invention to produce absorbent pads which may be individually conformed by the user so establish improved fit and comfort. It is a further object of this invention to produce absorbent pads at low cost. It is a another object of this invention to produce absorbent pads which can be disposed to assume a wide variety of body hugging conformations. It is yet another object of this invention to produce absorbent pads able to maintain such conformations. It is still another object of this invention to produce such absorbent pads having means of maintaining close proximity with contoured, fluid-bearing surfaces.

SUMMARY OF THE INVENTION

The form retentive absorbent pads of this invention comprise fluid absorbent material and at least one bendable element which can be deformed by the user and which will retain its shape during use. The absorbent pads of this invention have a body-facing side and an undergarment-facing side.

In one preferred embodiment, the bendable element comprises a strap extending transversely across the center of the pad. The strap is preferably shaped such that the portion contiguous with the undergarment-facing side of the pad is in a "double-concave" configuration. The strap ends which protrude from each longitudinal edge of the pad, or "winglets", are shaped in convex configuration. These winglets are designed to be bent around the edges of the crotch portion of an undergarment.

In a second embodiment, the strap has a uniform width to provide greater central strength and conformability. In third and forth embodiments, the bendable elements extend along opposing longitudinal edges of the central region, to provide a degree of conformability in the longitudinal (y axis) direction. The third embodiment comprises multiple bendable convex winglets or fingers which are individually bendable around the edge of the undergarment to retain the pad in place. In the fourth embodiment, the bendable elements are embedded within the pad.

As seen from the above, the bendable element(s) of the preferred embodiments may be affixed to an outer surface of the fluid absorbent material, in which case they are preferably adapted to further provide a degree of attachment to the undergarment, or may be embedded within the fluid absorbent material of the pad, in which case they serve only the function of providing the desired conformability.

DESCRIPTION OF THE PREFERRED EMBODIMENTS

The pads of the present invention provide superior fit and conformability to body shape through the utilization of at least one bendable element disposed in the central region of the pad. In particular, absorbent feminine products are provided which comprise an elongate pad having a body facing side and an undergarment facing side, and defining longitudinal edges, said pad comprising fluid absorbent material. These products further comprise bendable means attached to said pad which can be bent by user for changing the shape of the pad when so bent, at least along the longitudinal axis of the pad.

Figure 1:
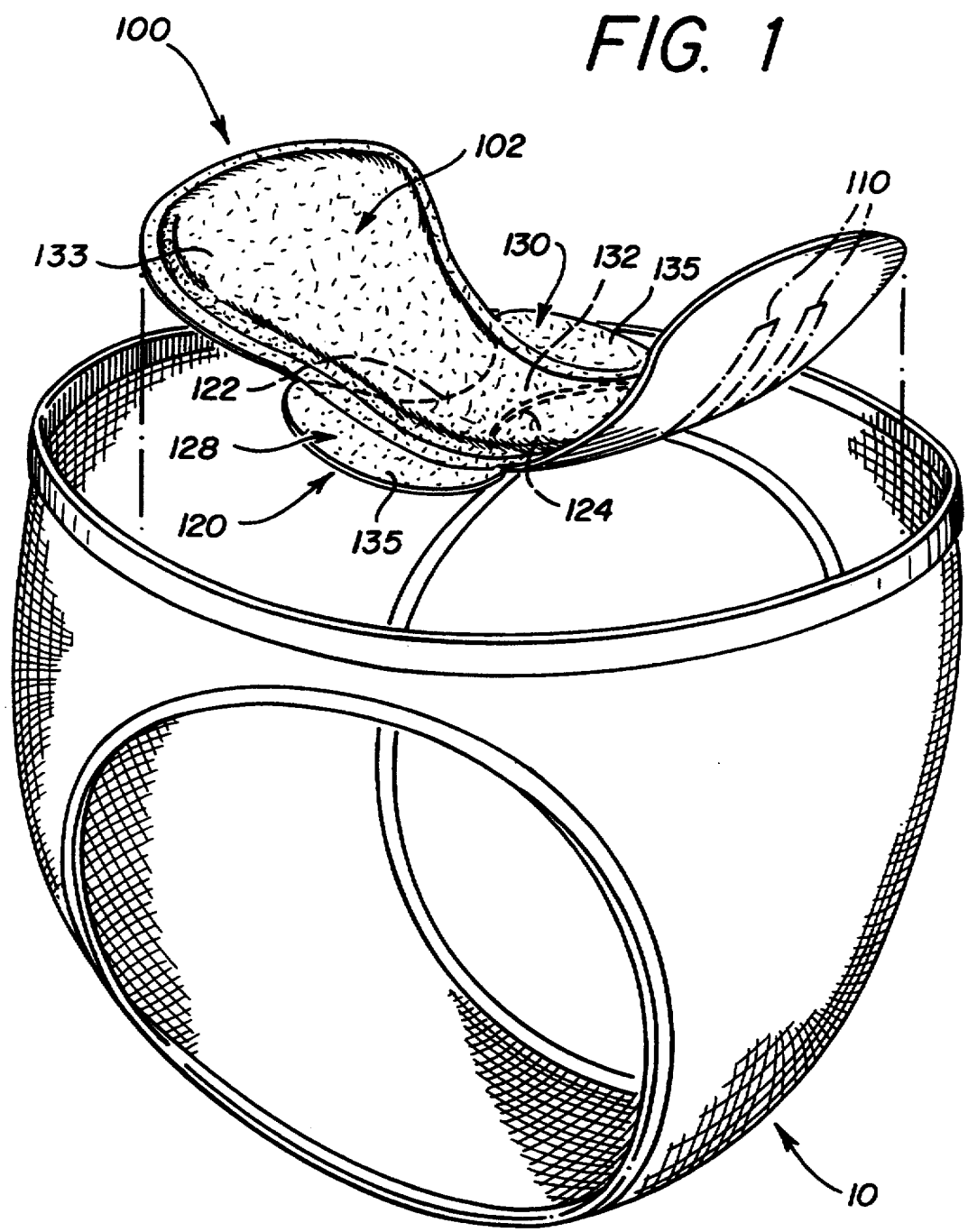
FIG. 1 is a perspective representation of a first embodiment of the present invention illustrating its insertion into an undergarment.

As seen in FIG. 1, pads such as pad 100, are designed to be placed in the interior crotch region of an undergarment, such as undergarment 10. FIG. 1 shows the insertion of the first embodiment of the pad of the present invention into its worn position in the undergarment. This embodiment generally comprises an elongated body, designated generally 102, which is typically somewhat narrower in its central region than at its ends. The pad may comprise additional conventional adhesive strips 110 to assist in attaching the pad to the undergarment, to prevent its rotation in place. In its simplest form, the pad comprises a cover 133 which envelopes a central absorbent 134 (shown in FIG. 3). The embodiment of FIG. 1 further comprises a central double concave strap, designated generally 120, which terminates at both ends in convex winglets which are bendable around the edges of the crotch portion of the undergarment.

Figure 4:
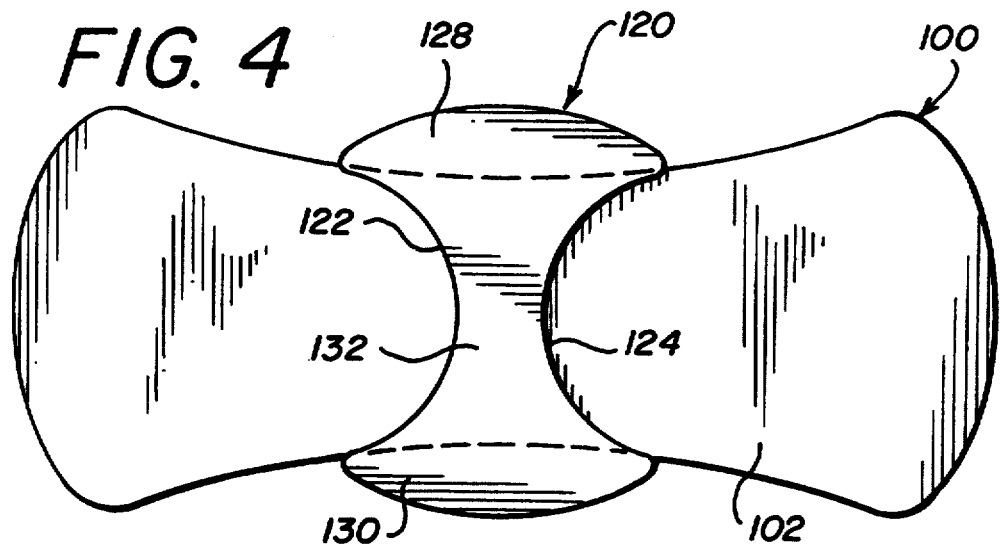
FIG. 4 is a bottom plan view of the embodiment of FIG. 1, showing its shape prior to engagement with the crotch portion of the undergarment.

The preferred shape of the strap is best seen in FIG. 4, wherein the concave edges 122 and 124 are illustrated as extending across the undergarment facing surface of the pad, to define a bendable strap 132 which has is greatest width at the edges of the pad, at which location the bases of the bendable winglets are formed. The winglets 128 and 130 are themselves convex, thus providing for the greatest overlap in their central regions when bent into place, while ensuring that no sharp edges will be created which could cause discomfort to the user. The strap 132 is generally disposed on the garment facing side of the pad, although it is within the scope of the present invention to cover all or at least a portion of the bendable element with a cover, if so desired. In any event, the bendable element should be disposed on the garment facing side of the bulk of the absorbent material which comprises the pad.

The bendable elements may be adhered by heat sealing, application of hot melt adhesives, emulsions or they may be layered between the barrier and absorbent layers.

Figure 2:
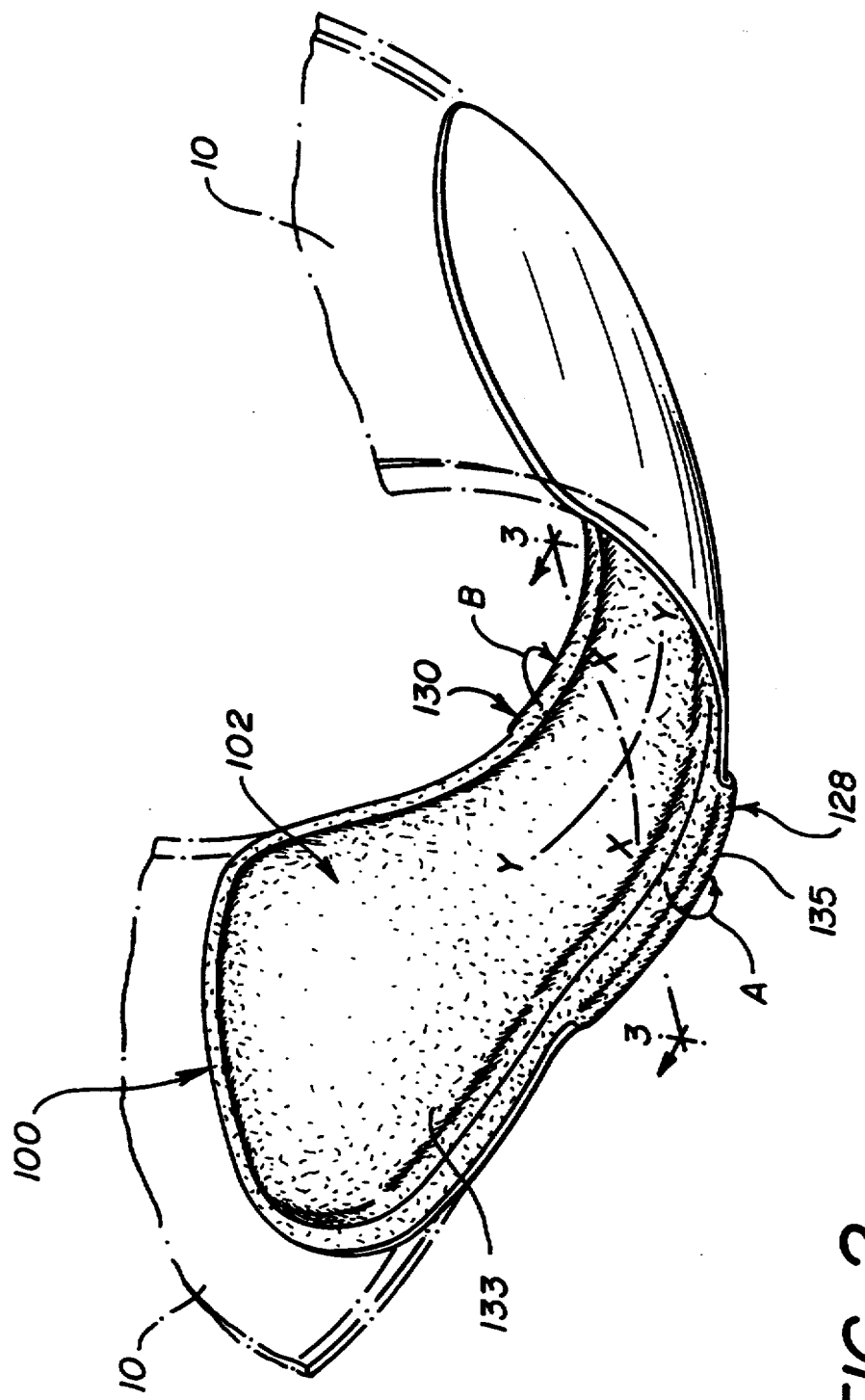
FIG. 2 is a perspective view of the embodiment of FIG. 1 showing the engagement of the pad with the central, crotch area of the undergarment; upper portions of the undergarment has been omitted from the figure.
Figure 3:
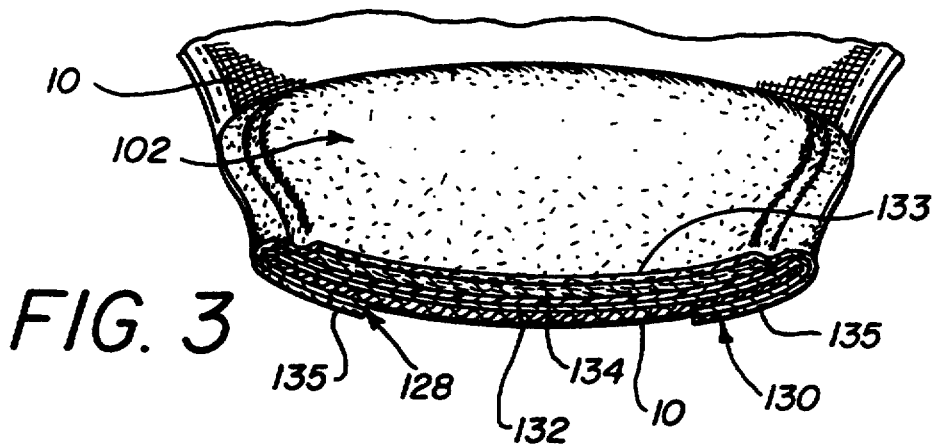
FIG. 3 is a cross-sectional view of the embodiment of FIG. 1, taken as indicated by the lines and arrow 3—3 in FIG. 2, showing the engagement of the undergarment by the pad.
Figure 5:
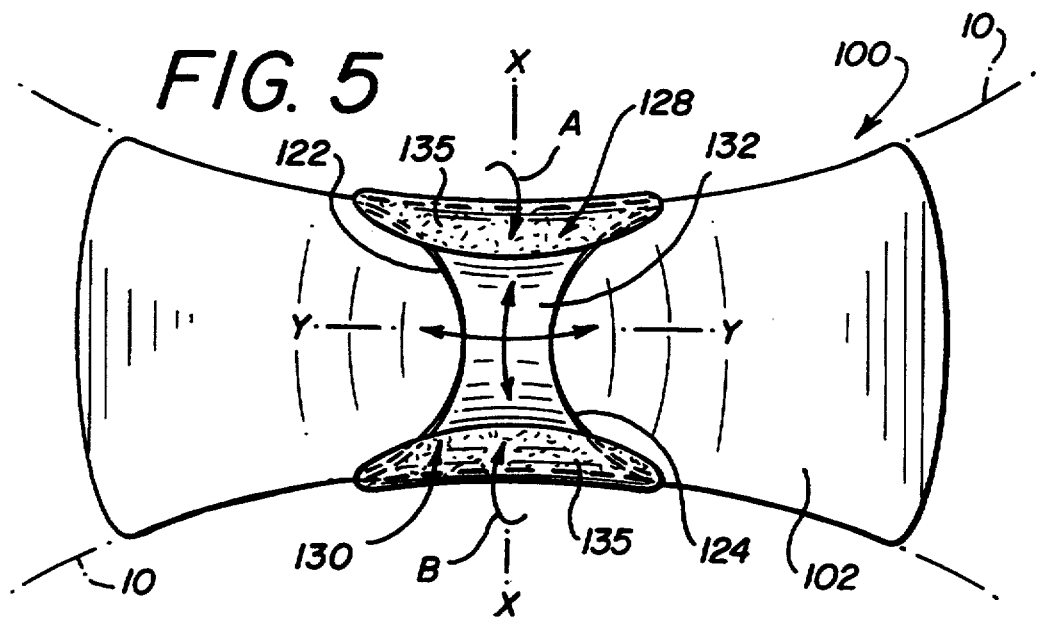
FIG. 5 is a bottom plan views of an embodiment of FIG. 1, showing the pad with the bendable elements bent into shape to retain the pad in place during use.

FIGS. 2, 3 and 5 illustrate the positioning of the pad in use. In FIG. 2 and 5, the arrows A and B illustrate the bending of the winglets into place to retain the pad around the edges of the undergarment. As seen from the texturing in FIG. 5, the bendable element is covered with a cover 135, such as a cover of thin non-woven material or plastic, as illustrated, to provide a non-irritating surface in the body contacting edges. As seen particularly in FIGS. 2 and 5, the bendable element is also bendable in the longitudinal (y) direction as well as in the transverse (x) direction. Since the strap is adhered to the body of the pad across its entire surface, the pad will change its shape in response to the bending of the bendable element. Once the winglets are bent around the edges of the undergarment, therefore, it is possible to bend the resulting "assembly" into any of a variety of shapes to conform it to the shape which is desired by the user.

In the simplest embodiment, the cover 132 envelopes the central absorbent 134. Those of ordinary skill in the art will recognize that a variety of absorbent, or layers of absorbent, may be used in a pad of this type. Examples of such absorbent include conventional pulp or peat materials, as well as more modern absorbent, such as superabsorbent powders. It will be appreciated by those of skill in the art that the principal requirements of such materials are that they efficiently absorb fluid and be amenable to the affixing or embedding of form retentive shaped bodies.

The materials useful for creating the bendable element of the products of this invention include any material capable of being bent and remaining in said bent position. Such materials include metal foils, waxes, impregnated nonwovens, polymer composites, laminated foils, foils sandwiched between polymer films, thermosettable polymers and the like.

Figure 6:
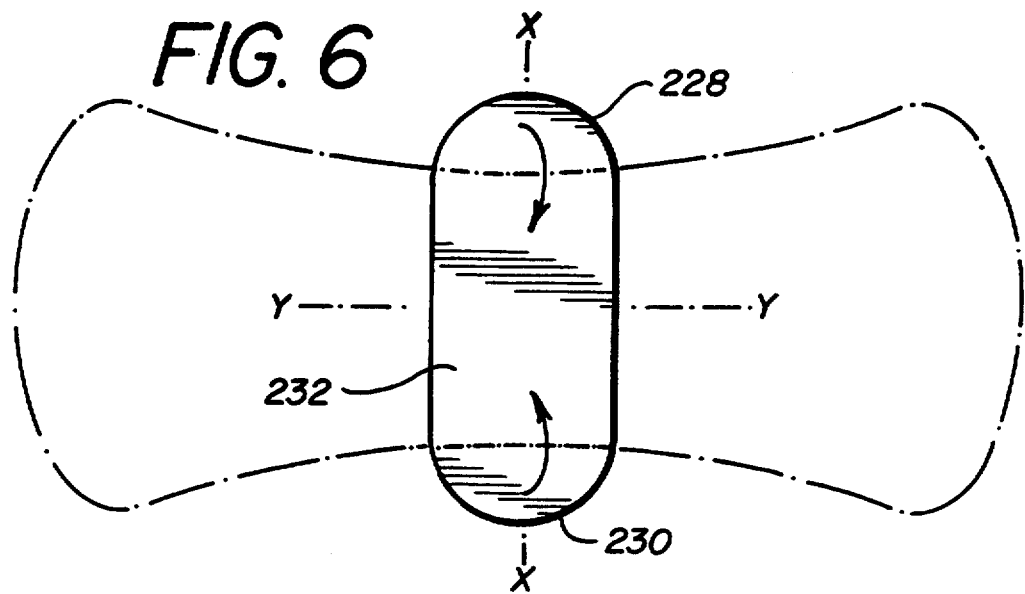
FIG. 6 is a bottom plan view of an embodiment of this invention having rounded, protruding members provided by transversely affixing a suitably shaped portion aluminum foil to absorbent material; the figure reveals the manner in which said members might be manipulated to engage an undergarment.

FIG. 6 illustrates an alternate embodiment of the present invention wherein the bendable strap 232 has a uniform width across the surface of the pad, shown in phantom in this view. Once again the strap terminates in convex winglets 228 and 230. Unlike the embodiment of FIGS. 1-5, however, the winglets do not exceed in longitudinal length the width of the strap. The embodiment of FIG. 6 provides for a greater degree of shaping in the central area, but a somewhat reduced ability to shape the pad along greater distances along the length of the pad. In this embodiment, the winglets are also bendable around the edges of the undergarment to affix it in place.

Figure 7:
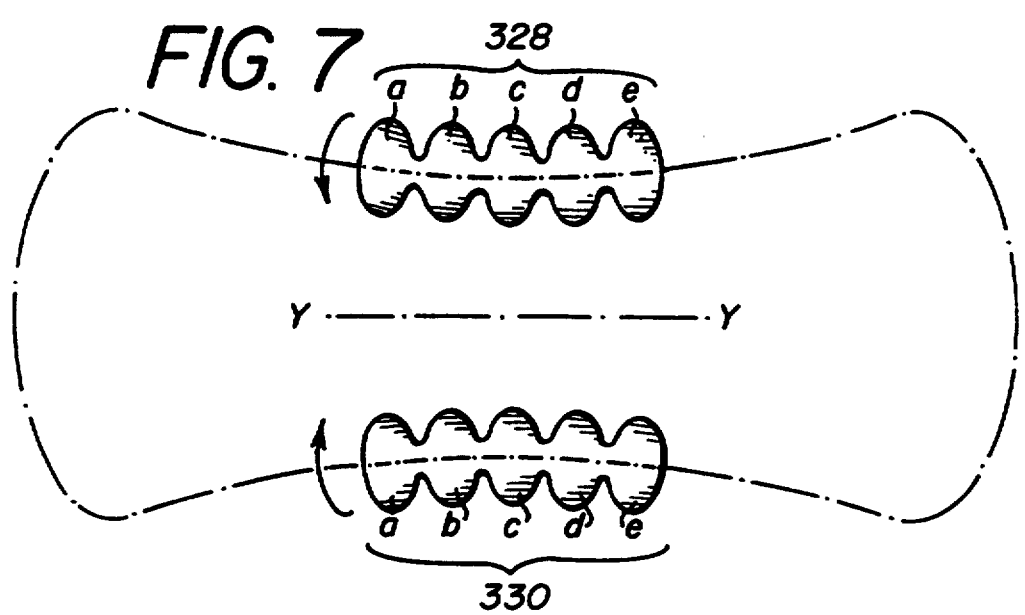
FIG. 7 is a bottom plan view of an embodiment of this invention having protruding, finger-shaped members provided by transversely affixing a suitably shaped portion aluminum foil to absorbent material; the figure reveals the manner in which said members might be manipulated to engage an undergarment.

In FIG. 7, a third embodiment pad is illustrated which comprises a plurality of winglets 328 a, b, c, d, & e and 330 a, b, c, d, & e for bending around the edge of the undergarment. In this embodiment, each winglet is a bendable finger of material. The advantage of this construction is that the longitudinal edges may be bent along a curved line so as to conform to the edges of an undergarment crotch. Unlike the embodiments of FIGS. 1-6, in this embodiment there are two distinct bendable members disposed along transverse edges of the pad. The primary function of the winglet system of FIG. 7 is to extend and improve upon the longitudinal extent of the bendable attachment means. Significantly also, however, the winglet system allows flexibility of the overall product in the "x" (i.e. transverse) and "z" (i.e. axial with the body of the user) directions. The greater the extent of scallop depth will correspondingly increase flexibility along these axes, with resulting improved conformability with the body of the user.

Also, the pad engaging portions of these members is similarly scalloped to aid in their attachment to the pad by providing expanded surface area without excessive material usage. The area between the winglets and the scalloped pad engaging portion of the bendable elements defines a fold line, which is where the fold will occur when the winglets are bent around the panty edges. In this embodiment, relatively greater y axis conformability is achieved, albeit with little or no contribution to conformability in the x direction. Additionally, a relatively greater distance along the panty edge will be covered and engaged by the bendable elements, which themselves are configured to easily conform to the desired shape by reason to the scalloping of both of the edges thereof.

Figure 8:
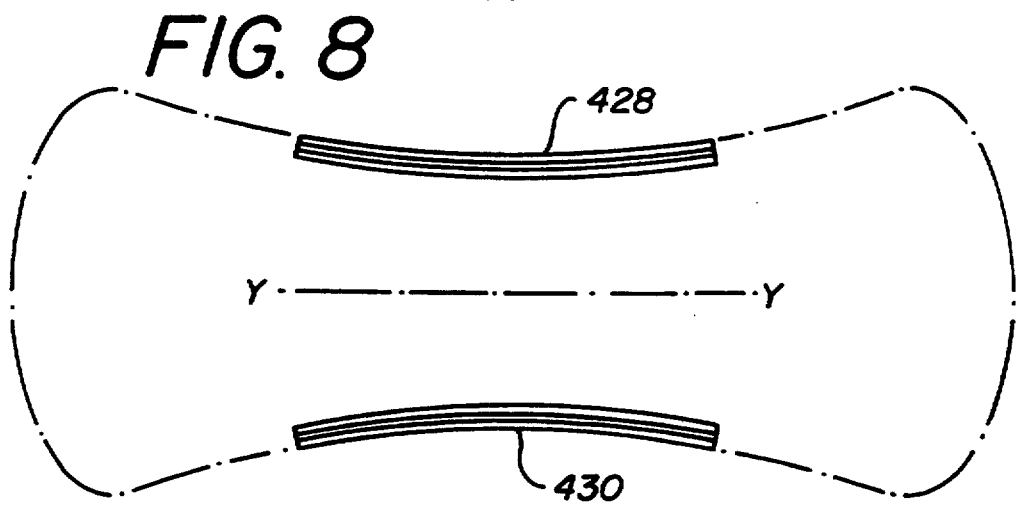
FIG. 8 is a bottom plan view of an embodiment of this invention having a segment of plastic coated metal wire affixed to opposite peripheral edges of absorbent material.

FIG. 8 illustrates a fourth embodiment wherein the pad comprises bendable wire stays 428 and 430. Bendable wire stays 428 and 430 function to hold the shape of the perineum and thereby retain the position of the pad. The features of the FIG. 8 embodiment are optionally compatible with those of the embodiment shown in FIG. 7. For safety purposes, these stays 428 and 430 are encased in a protective wrapping, such as paper or plastic, to ensure that even if they somehow were to penetrate the cover of the pad to become exposed, they still would not produce injury to the wearer. These bendable wires are not themselves dissimilar to conventional bag ties currently used to tie plastic garbage bags. Their purpose is to provide conformability in the y and z directions when embedded in the pad in proximity to the longitudinal edges of the pad, which is shown in phantom in FIG. 8.

It will be appreciated by those of skill in the art that the present invention may be practiced with a wide variety of bendable elements and absorbent and covering materials. Such elements may comprise any material which may be readily manipulated into a desired conformation and which tends to retain that conformation. Malleable metals, such as aluminum, tin, or copper, alloys thereof, and plastics, as hereinbefore mentioned, provide good examples of such materials; it is preferred that a malleable metal, such as aluminum, or an alloy thereof be employed in the practice of the present invention.

The bendable elements of the present invention may be fabricated from such materials by various means, such as extrusion, cutting, and stamping, as well known to those of skill in the art. Preferred shapes for such materials are given in FIGS. 4, 5, 6, 7 and 8, and additionally include wires or tubes, corrugated sheets, laminates, and the like.

Alternatively, attachment means can comprise a thermodeformable material such as a wax on the surface of the form retentive absorbent pad; said material would adhere to a second shaped body such as undergarment in the presence of body heat.

The bendable elements of the present invention can be attached to or embedded within the body of the pad by various means. Such means include conventional adhesives, sewing, and/or stapling. It is preferred that the shaped body be affixed to fluid absorbent material by a water insoluble adhesive.

The present invention will be further understood by reference to the drawings and to the example(s) given below, all of which are given for illustrative purposes only and are not limitative.

What is claimed is:

1. An absorbent feminine absorbent product comprising:
    an elongate pad having a longitudinal axis and a transverse axis, a body facing side and an undergarment facing side, and defining longitudinal edges, said pad comprising fluid absorbent material; and
    bendable means comprising a strap of bendable material extending transversely across a central portion of said pad and a plurality of winglets extending beyond the transverse edges of said pad, the shape of said strap being double concave in the direction transverse of the pad, said bendable material being capable of being manipulated into a desired conformation and tending to retain that conformation, said winglets shaped so that they are generally convex in relation to the pad and bendable around the edges of an undergarment to hold said product in place in the undergarment during use, said bendable means being attached to said pad such that said bendable means can be bent by a user for changing the shape of the pad when so bent at least along the longitudinal axis of the pad, said bendable means when bent remaining in said bent position during use without the use of extrinsic mechanisms.

2. An absorbent feminine absorbent product comprising:
    an elongate pad having a longitudinal axis and a transverse axis, a body facing side and an undergarment facing side, and defining longitudinal edges, said pad comprising fluid absorbent material;
    bendable means attached to said pad comprising a material which may be manipulated into a desired conformation and which tends to retain that conformation, such that said bendable means a are bendable to impart a concave curvature to at least said body facing side of said pad along at least one of said axes, thereby causing at least said body facing side of said pad to retain said concave curvature during use without the use of extrinsic mechanisms; and
    a plurality of winglets extending beyond the transverse edges of said pad;
    wherein said bendable means comprises a strap of bendable material extending transversely across a central portion of said pad and said plurality of winglets, said winglets being bendable around the edges of an undergarment to hold said product in place in the undergarment during use.

3. The product of claim 2, wherein said winglets are shaped such that they are generally convex in relation to the pad.

4. The product of claim 2, wherein said bendable means forms bent edges extending substantiality parallel to said longitudinal axis of said pad when said winglets are bent around edges of an undergarment and wherein said pad further comprises a cover, said cover extending over at least a portion of said bendable means so as to extend over said bent longitudinal edges of said bendable means when said winglets are bent around edges of an undergarment.

5. The product of claim 2, wherein said bendable means comprises a strap of metallic foil.

6. The product of claim 2 wherein said bendable means is embedded within said pad.

7. The product of claim 6 wherein said bendable means comprises a longitudinal element embedded within said pad.

8. The product of claim 7, wherein said bendable means comprises at least one wire stay.

9. The product of claim 8 wherein said wire stay comprises a wire encased in a protective sheath.

10. The product of claim 2 wherein said bendable means comprises a plurality of bendable element attached along each longitudinal edge of said pad, defining a plurality of bendable winglets disposed along each longitudinal edge of said pad, said winglets being sized for bending over the edges of the undergarment when the pad is in use.

11. The invention of claim 10, wherein said bendable elements are generally scalloped shaped to define fingers of attachment of said bendable elements to said pad.

12. The invention of claim 2, further comprising adhesive means for attaching the bendable means to said pad.

13. The product of claim 2 wherein said bendable means comprises a malleable material.

14. The product of claim 2, wherein said at least one of said axes along which said concave curvature is imparted to at least said body facing side is said longitudinal axis.

15. The product of claim 1, wherein said at least one of said axes along which said concave curvature is imparted to at least said body facing side is said transverse axis.

16. The product of claim 1, wherein said bendable means is bent so as to impart a concave curvature to at least said body facing side of said pad along both said longitudinal axis and said transverse axis.

17. The product of claim 2, wherein said bendable means is attached to said garment facing side of said pad.

18. The absorbent product according to claim 1, wherein said means for attaching said strap to said pad comprises bonding said strap to said undergarment facing side.

19. The absorbent product according to claim 18, wherein said strap is bonded to said undergarment facing side by heat sealing.

20. The absorbent product according to claim 18, wherein said strap is bonded to said undergarment facing side by adhesive.

21. The absorbent product according to claim 1, wherein said strap has a surface conforming to said shape into which said strap is bent, and wherein said means for attaching said strap to said pad comprises attaching said strap to said pad across substantially the entirety of said surface.

22. The absorbent product according to claim 1, wherein said shape of said strap imparts a concave curvature to at least said body facing side of said pad along both said longitudinal and transverse axis.

23. The absorbent product according to claim 1, wherein said shape into which said strap is bent comprises a concave curvature along first and second perpendicular directions.

* * * * *